United States Patent [19]

Gordon et al.

[11] 4,064,230

[45] Dec. 20, 1977

[54] POLYENIC MACROLIDE COMPOSITIONS

[75] Inventors: Harry W. Gordon, Bronx, N.Y.; Carl P. Schaffner, Trenton, N.J.

[73] Assignee: Schmid Laboratories, Inc., Little Falls, N.J.

[21] Appl. No.: 731,000

[22] Filed: Oct. 8, 1976

Related U.S. Application Data

[60] Division of Ser. No. 560,628, March 21, 1975, Pat. No. 4,000,254, which is a division of Ser. No. 80,509, Oct. 13, 1970, Pat. No. 3,891,752, which is a continuation-in-part of Ser. No. 769,919, Feb. 5, 1969, abandoned, which is a continuation-in-part of Ser. No. 623,847, March 17, 1967, Pat. No. 3,584,118, which is a continuation-in-part of Ser. No. 544,712, April 25, 1966, abandoned, and a continuation-in-part of Ser. No. 838,706, July 2, 1969, abandoned.

[51] Int. Cl.² .................. A61K 9/52; A61K 9/30; A61K 35/00

[52] U.S. Cl. ............................. 424/19; 424/23; 424/115

[58] Field of Search .................. 424/115, 23, 19

[56] References Cited

PUBLICATIONS

Chem. Abst. 8th Coll. Index vol. 66–75 (1967–1971) p. 14435s.

Primary Examiner—Sam Rosen
Attorney, Agent, or Firm—Darby & Darby

[57] ABSTRACT

A method of increasing the overall effectiveness, including stability and gastrointestinal tolerability, of a polyenic macrolide selected from the class consisting of candicidin, fungimycin, hamycin and mediocidin is described which comprises orally administering the polyenic macrolide with an absorbent material. Compositions containing a polyenic macrolide and a suitable absorbent material preferably in beadlet form are described for use in treating various conditions including prostate hypertrophy, hypercholesterolemia and acne.

14 Claims, No Drawings

POLYENIC MACROLIDE COMPOSITIONS

This application is a division of application Ser. No. 560,628 filed Mar. 21, 1975, now U.S. Pat. No. 4,000,254, which is a division of application Ser. No. 80,509, filed Oct. 13, 1970, now U.S. Pat. No. 3,891,752, which is a continuation-in-part of application Ser. No. 769,919, filed Feb. 5, 1969, now abandoned, which is a continuation-in-part of application Ser. No. 623,847, filed Mar. 17, 1967, now U.S. Pat. No. 3,584,118, which is a continuation-in-part of Ser. No. 544,712, filed Apr. 25, 1966, now abandoned; and a continuation-in-part of Ser. No. 838,706, filed July 2, 1969, now abandoned.

This invention relates to improving the effectiveness, stability and gastrointestinal tolerability of orally administered polyene macrolides and compositions containing such polyene macrolides.

In copending application Ser. No. 623,847 filed Mar. 17, 1967 there is described the oral administration of polyenic macrolides for the treatment of prostatic hypertrophy, and in copending application, Ser. No. 627,313, filed Mar. 31, 1967, there is described the oral administration of polyenic macrolides for treating hypercholesterolemia and preventing absorption of cholesterol from the intestinal tract. It has been found that some of the more active polyene macrolides (e.g. candicidin, fungimycin, hamycin) are somewhat unstable under the acidic conditions in the stomach and cause gastrointestinal disturbance (i.e. emesis and diarrhea) in some patients. This has hindered achieving the optimum levels of overall effectiveness for these polyenic macrolides by the oral route of administration in their use for treatment of the foregoing conditions.

It has now been discovered that the overall effectiveness including stability and gastrointestinal tolerability of certain polyenic macrolides administered orally can be increased by co-administering such materials with an absorbent material.

Accordingly, one aspect of the present invention is to increase the stability and gastrointestinal tolerance of certain polyenic macrolides.

Another aspect of the present invention relates to a polyenic macrolide composition containing an absorbent material which binds or has an affinity for the polyenic macrolide in an acidic environment and releases the polyenic macrolide in a substantially neutral pH environment.

Still another aspect of the present invention relates to polyenic macrolide compositions which exhibit optimum effectiveness and tolerability in the treatment of prostate hypertrophy, hypercholesterolemia, acne, intestinal moniliasis and other related conditions.

A further preferred aspect of the present invention relates to compositions in beadlet form containing the polyenic macrolides of the present invention.

An additional aspect of the present invention relates to the process of manufacturing the beadlets containing the polyenic macrolides of the present invention.

These and other aspects of the invention will be apparent from the foregoing description.

The compositions of the present invention have numerous uses including the treatment of prostatic hypertrophy, treatment of hypercholesterolemia, regulation of cholesterol absorption in dietary control, acne treatment, etc. The polyenic macrolides described belong to the hexaene and heptaene class of polyene macrolides described in the prior art literature and patents and are selected from the class consisting of candicidin, fungimycin, hamycin and mediocidin.

The heptaene polyene macrolides claimed herein are classifiable into two groups which may be correspondingly identified as follows:

A. Aromatic I — of which candicidin and hamycin are examples consisting of the heptaene macrolide nucleus, one carboxyl group, a single amino sugar moiety (mycosamine) glycosidically linked to the macrolide nucleus and an aromatic amino moiety (p-aminophenyl) aldolically linked to the macrolide nucleus.

B. Aromatic II — of which fungimycin is an example, consists of the heptaene macrolide nucleus, an aromatic amino moiety (N-methyl-p-aminophenyl), aldolically linked to the macrolide nucleus, and an amino sugar (perosamine), glycosidically linked to the macrolide nucleus. It is noted that the aromatic amino moiety just identified has previously been incorrectly reported in the literature as a p-aminobenzyl moiety.

The polyenic macrolide mediocidin belongs to the hexaene class of polyene macrolides that have been described in the literature. Its structure has not yet been sufficiently characterized as to all the substituents linked to the polyenic macrolide nucleus.

The following articles may be consulted for references to the discovery, isolation and chemical properties of the polyenic macrolides:

1. Vining, "The Polyene Antifungal Antibiotics" Hindustan Antibiotics Bull., Vol.s.pp 32–54 (1960)
2. Waksman et al, "The Actinomycetes, Vol. III, Antibiotics of Actinomycetes" (Williams and Wilkins, Baltimore, 1962)
3. Droughet, "Noveaux Antibiotiques Antifongiques" Symp. Int. Chimiotherapie, Naples, 1961, pp 21–50 (1963).
4. W. Oroshnik et al, "Fortschritte der Chemie Organischer Naturstoffe" Vol. XXI, pp 18–79 (1963).

Although the specific polyenes named supra, are identified and described in the literature, references are given here for abundance of identification to various patents and well known publications. Thus, candicidin is described in U.S. Pat. No. 2,992,162 issued July 1, 1961; "Physician's Desk Reference" (19th Edition 1964); and the "Merck Index of Chemicals and Drugs" (7th Edition).

Fungimycin is described in U.S. Pat. No. 3,182,004, issued May 4, 1965 and the "Merck Index of Chemicals and Drugs" (8th Ed.);

Hamycin is described in U.S. Pat. No. 3,261,751 issued July 19, 1966 and in "Martindale's Extra Pharmacopedia" (25th Ed.) published Feb. 1067.

Mediocidin is available from the culture collection at the Institute of Microbiology, Rutgers University.

It will be understood that where a polyenic macrolide compound described in the art is identical with one of the above specifically named polyenic macrolide compounds, but has been known by another name by reason of independent production or production in accompaniment to other antibiotics, the identification of such substances by the name set forth above is intended to mean the same compound under all other designations.

The polyenic macrolides described supra are administered by the oral rote in combination with an absorbent material. The absorbent material binds or has an affinity for the polyenic macrolide under the acidic conditions that exist in the gastrointestinal tract and releases the polyenic macrolide (i.e. loses its binding affinity therefor) in a substantially neutral pH (6 to 7).

The selection of the absorbent material to be coadministered with the polyene macrolide should be one that is non-toxic, pharmaceutically acceptable for oral use, and is capable of binding under acidic conditions in a pH range of about 3 to 5 and releasing the polyene macrolide in a substantially neutral pH environment. The absorbent material may be either organic or inorganic in character. The inorganic materials are preferably salts or bases of divalent or trivalent metals. Thus the cation portion of the inorganic absorbent material may be a metal such as calcium, aluminum, magnesium, bismuth, iron, etc., with calcium being the preferred cation. The anion portion of the inorganic absorbent material may be a carbonate, a phosphate, a sulfate, a silicate or a hydroxide, with a carbonate being preferred. Illustrative of the specific inorganic absorbent materials are calcium carbonate, calcium phosphate, hydrated aluminum silicate, aluminum hydroxide, magnesium oxide, magnesium carbonate, magnesium trisilicate, magnesium hydroxide, bismuth subcarbonate, aluminum phosphate, etc. Suitable organic absorbent materials include cellulose derivatives such as sodium carboxy methyl pectin, starches (e.g. barley, arrowroot), gums (acacia, tragacanth), ion exchange resins (e.g. a polyamine methylene resin), etc.

The absorbent material is preferable mixed with the polyenic macrolide and thereafter formulated into a solid form suitable for oral administration. The proportion of absorbent material to polyenic macrolide per unit dose is about 8:1 to about 2:1. The preferred ratio is about 4:1 based on the activity of the polyenic macrolide by weight. The oral dose may take the form of a tablet, capsule, pill, beadlet or other solid dosage unit. It has been found that the optimum effectiveness and highest tolerability and stability of the polyenic macrolide is achieved when the oral dose is in beadlet form. As used herein "beadlet" means beads, granules, pilules or any micro solid dose form contained in a capsule, preferably hard shell.

It has also been found desirable to incorporate a pharmaceutically acceptable acidic material in the polyenic macrolide containing composition where the pH of the polyenic macrolide is substantially on the alkaline side. The inclusion of the acidic material will further increase the tolerability of the polyene by providing a composition having a pH in the neutral range. Thus, in the case of candicidin, which has a pH of about 10, it is desirable to bring the pH down to 6.5 to 7.5 with an acidic material such as potassium phosphate (monobasic). Generally, the ratio of acidic material to candicidin used in each unit dose is between about 1:1 to 2:1. Other acidic materials may also be used such as citric acid, lactic acid, glycine, etc.

The active ingredient is preferably formulated to provide a sustained release coating. The use of a sustained release coating around each beadlet containing the active ingredient provides for a gradual step wise exposure of the polyenic macrolide to the gastrointestinal tract, thereby avoiding irritation that would occur if all of the active ingredient was exposed at the same time. As used herein "sustained release" means a coating which prevents substantially all of the polyenic macrolide from being released together with the absorbent material at a single time in the stomach and is intended to include enteric coating whereby substantially all of the medicament is released in the intestinal tract.

Generally, each unit dose of medicament contains between about 25 and 200 mg of active material.

The polyenic macrolides claimed herein may be compounded into the desired oral form in combination with other inert ingredients including fillers such as talc, lactose, starch, bentonite, diatomaceous earth etc.

A suitable procedure for preparing the beadlets is as follows:

In the preparative method, the powdered polyenic macrolide is dispensed, e.g. by dusting, on to a medicinally acceptable core material. Nonpareil seeds are preferably employed and it should be understood that while the nonpareil seeds will be referred to collectively as "core" each such nonpareil seed is in fact a separate core. Adhesion of the polyenic macrolide on the core is accomplished by spraying the core with an adhesive formulation in a non-aqueous solvent. The solvents used may be lower alcohol or halogenated hydrocarbons or mixtures thereof. The criteria for the selection of the solvent is the ease with which the solvent volatilizes and can therefore be removed rapidly without heating.

A typical suitable adhesive formulation comprises a non-aqueous solution containing shellac, polyvinyl pyrrolidone and ethyl alcohol. Other non-aqueous adhesives may be employed such as ethyl cellulose, polyethylene glycol 4000, polyethylene glycol 6000, sodium carboxy methyl cellulose.

Thus the first step of the method involves spraying of a non-aqueous adhesive solution on the core and the second step involves dusting of the polyenic macrolide onto the sprayed core. The polyenic macrolide which at this stage in the process may be in admixture with the selected absorbent material, e.g. calcium carbonate, is spread onto the core using an atomizer. This procedure is carried out by continuous rotation of the coating pan during the time that the polyenic macrolide formulation is being added. Rotation of the pan is continued until all of the alcohol has been evaporated from the adhesive formulation. Evaporation of the alcohol should not be carried out at an elevated temperature because heat may alter or destroy the activity of the polyenic macrolide. The procedure of adhering the polyenic macrolide to the core is repeated at least nine times using the adhesive formulation as indicated above. After the last coat has been adhered to the core, the core is air dried at room temperature. The resulting formulation provides a product wherein the polyenic macrolide is gradually released in the gastrointestinal track in combination with the absorbent material.

If an enteric coat is desired, an appropriate number of edible enteric coatings are overlaid on the polyenic macrolide-coated core to provide a composition that will be identified hereafter as an "enteric coated" beadlet. The number of enteric coats that will be applied can be varied and obviously a fewer or greater number of coats can be applied to afford the desired modifications in the release characteristics of the formulation.

The enteric coating procedure should be carried out in a non-aqueous system and the enteric coated film forming material may be any one of the conventional materials used for such purposes which are described in the prior arts such as shellac, waxes, fatty acids, fatty alcohols, high molecular weight glycerine esters, film forming polymers, fats or a combination of any of one or more of these coatings. Illustrative of substances that may be used for this purpose is cellulose acetate phthalate with resinous carrier; cellulose acetate phthalatetolu balsam-shellac; cellulose acetate phthalate with fats and waxes; shellac-castor oil; ammoniated shellac; shellac-stearic acid-tolu balsam; stearic acid-castor oil over shellac-silica gel, cellulose acetate phthalates with or without plasticizer and dusting power(s); acid phthalates of glucose, fructose, etc.; ternary copolymers of styrene, methacrylic acid and butyl half-ester of maleic acid; alkyl resin-unsaturated fatty acids-shellac; polyvinyl acid phthalate, etc.

The enteric coated film is applied to the beadlets by spraying a solution of the selected film forming material on to the beadlets after which the beadlets are permitted to air dry with continuous rotation of the pan in which they are contained. This procedure is repeated until the selected number of enteric coats have been applied to the beadlets. In general, the coating technique involves using conventional equipment. The coating process involves placing an appropriate number of coated beads in a standard coating pan followed by the addition thereof of a sufficient quantity of the coating composition to wet the beads. The rotation of the pan is continued until all the coating composition has been absorbed by the cores. During the coating operation room temperatures are maintained. After the first coating operation is completed, the beadlets are air dried and thereafter the remaining coats are applied in a similar manner.

The polyenic macrolide beadlets after enteric coating are then passed through a No. 12 mesh sieve discarding any oversize. Thereafter the beadlets are passed through a No. 16 mesh sieve discarding the undersize. Hard shell capsules are filled with the remaining coated beadlets in the range of 1200 to 1700 microns each in size. The number of beadlets to be incorporated into a single hard shell capsule is a variable that is determined by the levels of active ingredients which are desired in the final product. The number of beadlets needed to achieve such level will depend upon the amount of medicine present in the individual beadlets.

Generally, a sufficient number of beadlets are added to the capsule to provide a unit dosage containing from about 25 to 200 mg of polyenic macrolide.

The following examples illustrate the pharmaceutical formulations of the present invention.

EXAMPLE 1

One thousand hard gelatin capsules available from Eli Lilly & Co. (size 0) were each filled with 50 mg of micronized candicidin (200% activity) obtained from S. B. Penick & Co., 200 mg calcium carbonate, 50 mg potassium phosphate (monobasic) and sufficient lactose to bring each capsule to full volume (i.e. about 80 to 100 mg lactose). In preparing the formulation for filling the capsules all of the above-identified materials were passed through a No. 60 mesh sieve. The mixing of the materials was initally carried out in container or the like using a paddle to stir the materials. After all the materials for the thousand capsules had been mixed together, the contents of the container was placed in a blender and mixing was continued for about 2 hours to achieve a homogeneous formulation. Each capsule was then filled with this admixture to provide the quantity of each ingredient indicated, supra.

EXAMPLE 2

One thousand capsules containing enteric coated beadlets using candicidin as the active ingredient, were prepared as follows: The quantities of candicidin, calcium carbonate, potassium phosphate (monobasic) and lactose were blended together as described in Example 1. In this case, 60.5 gms (by activity) of candicidin (S. B. Penick & Co.), 220 gms calcium carbonate and 55 gms potassium phosphate (monobasic) were passed through a No. 60 mesh sieve and the contents of the sieve receptacle transferred to a blender. The resulting blended powder was then coated onto a sufficient number of nonpareil seeds placed in a coating pan (e.g. 10-12 micron size) using a 270 ml solution (divided into nine equal parts) of 50 ml shellac solution (5%) 10 gms polyvinyl pyrrolidone ("Plasdone 29-32") and 300 ml ethyl alcohol for adhering the formulation to the nonpareil seeds. This procedure was caried out by spraying 30 ml of this solution (using an atomizer) with a continuous rotation of the pan and adding 37.37 gms blended powder. Rotation of the pan is continued until the alcohol has evaporated. This procedure is repeated nine times to provide nine coats of candicidin around the nonpareil seeds. Thereafter 50 ml of a solution of shellac and ethyl alcohol are sprayed over the coated seeds with continuous rotation of the pan and the seeds are air dried.

The air dried seeds are placed in a clean coating pan and coated with 440 ml of a solution (divided into twenty equal parts) made up of 37.5 grams cellulose acetate phthalate, 150ml acetone, 212.5 ml ethyl alcohol, 9.37 ml diethyl phthalate and 118.75 ml methylene chloride, using 5 lbs. air pressure to spray. The coated seeds are air dried (room temperature) with continuous rotation of the pan. This procedure is repeated twenty times so that all 440 ml of the cellulose acetate phthalate solution is used. The coated seeds are then passed through a No. 12 mesh sieve, discarding any oversize. Then the seeds are passed through a No. 16 mesh sieve discarding the undersize. Capsules as described in Example 1 are then filled with the remaining coated seeds ranging in size from about 1200 to 1700 microns.

EXAMPLE 3

One thousand hard gelatin capsules available from Eli Lilly & Co. (size 0) were each filled with 50 mg micronized candicidin, 210 mg. lactose (USP), 90 mg glycine (USP) and 210 mg calcium carbonate (heavy USP). The candicidin, glycine and calcium carbonate were triturated together in a pestle and mortar until a very fine powder was obtained and then the lactose was added to this powder. Each capsule was then filled with this admixture to provide the quantity of each ingredient indicated above. Obviously, the quantity of active ingredient may be altered in each capsule as desired.

EXAMPLE 4

Eight thousand capsules containing candicidin as the active ingredient were prepared using 440 gm (by activity) of candicidin, 400 gm potassium phosphate monobasic (USP), 1600 gm calcium carbonate heavy (USP) and 1840 gm nonpareil seeds (1000 to 1200 microns). The nonpareil seeds are placed in a coating pan and sprayed with 220 ml of a shellac solution (hereinafter shellac solution "A") made up of a 80 gm shellac solution (6 lb. cut in solution) diluted with 280 gm anhydrous alcohol (using an atomizer and 5 lbs. air pressure) with a continuous rotation of the pan until the seeds are completely wet. Thereafter about 1/10 of the powder blend (291 gm) obtained by mixing the candicidin, calcium carbonate and potassium phosphate is slowly added to the pan, the pan being rotated until the powder completely adheres to the seeds. Additional ethyl alcohol is added to the pan to insure complete adherence of the powder onto the seeds and rotation is continued until the alcohol has been evaporated.

Following the foregoing coating operation there is sprayed onto the seeds with an atomizer using 5 lb. air pressure about 196 ml of a solution made up of 192 gms. shellac solution 120 grams polyvinylpyrrolidone and 1768 ml ethyl alcohol with continuous rotation of the pan until the seeds are completely rewet. The atomizer is then stopped and there is slowly added 1/10 of the powder blend of candicidin, calcium carbonate and potassium phosphate and rotation is continued until the powder completely adheres to the seeds. Thereafter ethyl alcohol is added to complete adherence of the powder to the seeds and the alcohol is evaporated. This coating process is repeated eight more times.

After the eight additional coats have been added, 220 ml of shellac solution "A" is sprayed onto the coated seeds using 5 lb. pressure with a continuous rotation of the pan until the solution is used up and the alcohol evaporated. The coated seeds are permitted to air dry and are then sieved through a No. 12 mesh sieve and the oversize seeds discarded. Then sieve the seeds through No. 16 mesh sieve the undersize seeds being discarded. Capsules as described in Example 1 are then filled with the remaining coated seeds having a size between about 1200 to 1700 microns to provide 50 mg of candicidin (by activity) per capsule.

The polyenic macrolides described herein are useful in treating prostate hypertrophy, hypercholesterolemia in mammals weighing at least one kilogram (e.g. dogs, humans, etc.). These uses have been described in the aforementiond copending application Ser. Nos. 623,847, & 627,313 and described in various literature publications subsequent to the filing of such applications. In view of the fact that the polyene macrolides bind with cholesterol in the intestinal tract and prevent absorption of cholesterol they are useful in dietary control and in treatment of conditions where it is desirable to control the quantity cholesterol absorbed into the blood stream. The polyenic macrolides also exhibit antiandrogen activity and are useful for treating conditions associated with androgen disorders, (e. g. acne).

The daily effective dose of the polyenic macrolide depends upon the condition being treated, the individual characteristics of each mammal being treated as well as the particular polyenic macrolide being used. Generally, the dose range is from about 1 mg to about 40 mg per kilogram of body weight per day for treatment of prostate hypertrophy and hypercholesterolemia. To prevent absorption of cholesterol a daily dose of between 1 mg to 15 mg per kg of body weight is effective whereas in treating androgen disorders the effective dose generally requires a minimum of 1 mg per kg of body weight. Clinical tests with candicidin have been effectively carried out to treat prostatic hypertrophy using a daily dose of between 2 and 10 mg. per kg. of body weight per day.

What is claimed is:

1. A composition comprising a capsule containing a multiplicity of beadlets, said beadlets together comprising (1) about 25 milligrams to about 100 milligrams of a polyenic macrolide selected from the class consisting of hamycin and mediocidin and (2) an absorbent material which binds with said polyenic macrolide in a substantially acidic pH environment and loses its affinity for said polyenic macrolide in a substantially neutral pH environment, the ratio of said polyenic macrolide to said absorbent material being about 1 to 2 to about 1 to 8.

2. A solid composition according to claim 1 wherin said absorbent material is selected from the group consisting of non-toxic inorganic material whose cation portion is selected from the class consisting of a divalent and trivalent metal and whose anion portion is selected from the group consisting of a carbonate, phosphate, silicate, sulphate and hydroxide.

3. A solid composition according to claim 1 wherein said cation is selected from the group consisting of calcium, magnesium, iron and aluminum.

4. A composition according to claim 1 wherein said polyenic macrolide is coated with a sustained release coating.

5. A solid composition according to claim 4 wherein said beadlets are contained in a hard gelatin shell capsule.

6. A solid composition according to claim 5 which includes an acidic material for maintaining the pH of said composition between about 6.5 and 7.5.

7. A formulation comprising a hard shell capsule containing a multiplicity of beadlets, said beadlets together comprising (1) about 25 to 100 milligrams of mediocidin, and (2) about 50 to about 400 milligrams of calcium carbonate, the ratio of mediocidin to calcium carbonate being no greater than about 1 to 2, said formulation having a pH between about 6.5 and 7.5.

8. A solid formulation according to claim 7 wherein said mediocidin is coated with a sustained release coating.

9. A solid composition according to claim 8 wherein said sustained release coating is an enteric coating.

10. A composition according to claim 7 which includes a potassium phosphate.

11. A formulation comprising a hard shell capsule containing a multiplicity of beadlets, said beadlets together comprising (1) about 25 to about 100 milligrams of hamycin, and (2) about 50 to about 400 milligrams of calcium carbonate, the ratio of hamycin to calcium carbonate being no greater than about 1 to 2, said formulation having a pH between about 6.5 and 7.5.

12. A solid formulation according to claim 11 wherein said hamycin is coated with a sustained release coating.

13. A solid composition according to claim 12 wherein said sustained release coating is an enteric coating.

14. A composition according to claim 12 which includes a potassium phosphate.

* * * * *